(12) United States Patent
Empfield et al.

(10) Patent No.: US 7,384,954 B2
(45) Date of Patent: Jun. 10, 2008

(54) 4-SUBSTITUTED IMIDAZOLES

(75) Inventors: James R. Empfield, Wilmington, DE (US); Eifion Phillips, Boothwyn, PA (US); Scott Throner, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/579,609

(22) PCT Filed: Nov. 15, 2004

(86) PCT No.: PCT/SE2004/001660

§ 371 (c)(1),
(2), (4) Date: May 17, 2006

(87) PCT Pub. No.: WO2005/049612

PCT Pub. Date: Jun. 2, 2005

(65) Prior Publication Data

US 2007/0105896 A1 May 10, 2007

(30) Foreign Application Priority Data

Nov. 19, 2003 (SE) .................................... 0303075

(51) Int. Cl.
*A01N 43/42* (2006.01)
*A61K 31/44* (2006.01)
*C07D 221/02* (2006.01)

(52) U.S. Cl. ...................... 514/299; 546/112
(58) Field of Classification Search ................ 546/112; 514/299
See application file for complete search history.

(56) References Cited

FOREIGN PATENT DOCUMENTS

| EP | 1219622 | * | 3/2002 |
| EP | 1219622 | A2 | 7/2002 |
| WO | 0215662 | A2 | 2/2002 |
| WO | 2004043960 | A1 | 5/2004 |

OTHER PUBLICATIONS

Araki et al., Japanese Pharmacological Society, "Neuronal nicotinic receptor and psychiatric disorders: functional and behavioral effects of nicotine", 2002, vol. 88, pp. 133-138.*
U.S. Appl. No. 10/579,608, James Empfield, et al.

* cited by examiner

*Primary Examiner*—Margaret D. Seamani
*Assistant Examiner*—Niloofar Rahmani
(74) *Attorney, Agent, or Firm*—Kenneth F. Mitchell; Michael A. Patane

(57) ABSTRACT

Compounds of formula I:

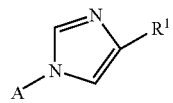

wherein A and $R^1$ are as defined in the specification, processes for preparing them, pharmaceutical compositions containing them and their use in therapy, especially in the treatment or prophylaxis of psychotic and intellectual impairment disorders.

10 Claims, No Drawings

4-SUBSTITUTED IMIDAZOLES

RELATED APPLICATIONS

This is a National Phase Application of PCT/GB2004/001659, filed Nov. 15, 2004, which claims the priority of Application No. 0303075-6 filed in Sweden on Nov. 19, 2003.

TECHNICAL FIELD

This invention relates to novel 4-substituted imidazoles or pharmaceutically-acceptable salts thereof, processes for preparing them, pharmaceutical compositions containing them and their use in therapy. This invention particularly relates to compounds that are ligands for alpha 7 nicotinic acetylcholine receptors (α7 nAChRs).

BACKGROUND OF THE INVENTION

The use of compounds which bind nicotinic acetylcholine receptors in the treatment of a range of disorders involving reduced cholinergic function, such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; and in Williams et al. (1994) "Neuronal Nicotinic Acetylcholine Receptors," Drug News & Perspectives, vol. 7, pp. 205-223.

DESCRIPTION OF THE INVENTION

This invention encompasses compounds of formula I:

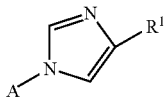

I wherein:

A represents:

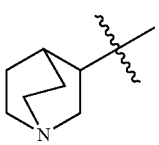

II

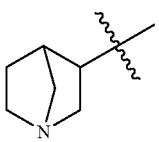

III

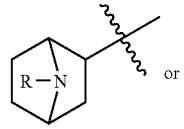 or

IV

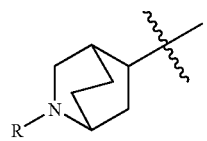

V where R represents hydrogen or methyl, and
$R^1$ represents hydrogen or a moiety of Formula VI

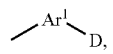

VI wherein:

$Ar^1$ is selected from a 5- or 6-membered aromatic or heteroaromatic ring having 0, 1 or 2 nitrogen atoms, 0 or 1 oxygen atoms, and 0 or 1 sulfur atoms, or selected from an 8-, 9- or 10-membered fused aromatic or heteroaromatic ring system having 0, 1, 2 or 3 nitrogen atoms, 0 or 1 oxygen atoms, and 0 or 1 sulfur atoms;

D is selected from hydrogen, $NR^2R^3$, or E-$Ar^2$;

wherein

E is a single bond, —O—, —S—, or —$NR^3$—;

$Ar^2$ is selected from a 5- or 6-membered aromatic or heteroaromatic ring having 0, 1 or 2 nitrogen atoms, 0 or 1 oxygen atoms, and 0 or 1 sulfur atoms;

where each $Ar^1$ or $Ar^2$ moiety may be unsubstituted or bear 1, 2 or 3 substituents selected from —$R^3$, —$C_1$-$C_6$alkyl, —$C_2$-$C_6$alkenyl, —$C_2$-$C_6$alkynyl, halogen, —CN, —$NO_2$, —$CF_3$, —$S(O)_nR^3$, —$NR^2R^3$, —$CH_2NR^2R^3$, —$OR^3$, —$CH_2OR^3$ OR —$CO_2R^4$;

$R^2$ and $R^3$ are independently selected at each occurrence from hydrogen, —$C_1$-$C_4$alkyl, aryl, heteroaryl, —C(O)$R^4$, —C(O)NH$R^4$, —$CO_2R^4$ or —$SO_2R^4$, or $R^2$ and $R^3$ in combination is —$(CH_2)_jG(CH_2)_k$— wherein G is oxygen, sulfur, $NR^4$, or a bond;

j is 2, 3 or 4;

k is 0, 1 or 2;

n is 0, 1 or 2, and $R^4$ is independently selected at each occurrence from hydrogen, —$C_{1-4}$alkyl, aryl, or heteroaryl.

The invention also encompasses stereoisomers, enantiomers, in vivo-hydrolysable precursors and pharmaceutically-acceptable salts of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

Compounds of the invention are those according to formula I:

wherein:
A represents:

I

II

III

IV

V where R represents hydrogen or methyl, and
R¹ represents hydrogen or a moiety of Formula VI

VI wherein:
Ar¹ is selected from a 5- or 6-membered aromatic or heteroaromatic ring having 0, 1 or 2 nitrogen atoms, 0 or 1 oxygen atoms, and 0 or 1 sulfur atoms, or selected from an 8-, 9- or 10-membered fused aromatic or heteroaromatic ring system having 0, 1, 2 or 3 nitrogen atoms, 0 or 1 oxygen atoms, and 0 or 1 sulfur atoms;
D is selected from hydrogen, $NR^2R^3$, or $E-Ar^2$;
wherein
E is a single bond, —O—, —S—, or —$NR^3$—;
Ar² is selected from a 5- or 6-membered aromatic or heteroaromatic ring having 0, 1 or 2 nitrogen atoms, 0 or 1 oxygen atoms, and 0 or 1 sulfur atoms;
where each Ar¹ or Ar² moiety may be unsubstituted or bear 1, 2 or 3 substituents selected from —$R^3$, —$C_1$-$C_6$alkyl, —$C_2$-$C_6$alkenyl, —$C_2$-$C_6$alkynyl, halogen, —CN, —$NO_2$, —$CF_3$, —$S(O)_nR^3$, —$NR^2R^3$, —$CH_2NR^2R^3$, —$OR^3$, —$CH_2OR^3$ or —$CO_2R^4$;
R² and R³ are independently selected at each occurrence from hydrogen, —$C_1$-$C_4$alkyl, aryl, heteroaryl, —C(O)$R^4$, —C(O)NH$R^4$, —$CO_2R^4$ or —$SO_2R^4$, or R² and R³ in combination is —$(CH_2)_jG(CH_2)_k$— wherein G is oxygen, sulfur, $NR^4$, or a bond;
j is 2, 3 or 4;
k is 0, 1 or 2;
n is 0, 1 or 2, and
R⁴ is independently selected at each occurrence from hydrogen, —$C_{1-4}$alkyl, aryl, or heteroaryl;
and stereoisomers, enantiomers, in vivo-hydrolysable precursors and pharmaceutically-acceptable salts thereof.

More particular compounds are those of formula I wherein:
A represents:

II

R¹ represents hydrogen or a moiety of Formula VI

VI wherein:
Ar¹ is selected from a 5- or 6-membered aromatic or heteroaromatic ring having 0 or 1 nitrogen atoms, 0 or 1 oxygen atoms, and 0 or 1 sulfur atoms;
D is selected from hydrogen, $NR^2R^3$, or $E-Ar^2$;

wherein:
E is a single bond, —O—, —S—, or —$NR^3$—;
Ar² is selected from a 5- or 6-membered aromatic or heteroaromatic ring having 0 or 1 nitrogen atoms, 0 or 1 oxygen atoms, and 0 or 1 sulfur atoms;
where each Ar¹ or Ar² moiety may be unsubstituted or bear 1, 2 or 3 substituents selected from halogen, —CN, —$NO_2$, —$CF_3$, —$CH_3$ or —$C_2H_5$;
R² and R³ are independently selected at each occurrence from hydrogen, —$C_1$-$C_4$alkyl, aryl, heteroaryl, or
R² and R³ in combination is —$(CH_2)_jG(CH_2)_k$— wherein G is oxygen;
j is 2, 3 or 4;
k is 0, 1 or 2;
and stereoisomers, enantiomers, in vivo-hydrolysable precursors and pharmaceutically-acceptable salts thereof.

Particular compounds of the invention are compounds according to formula I wherein A represents:

II and stereoisomers, enantiomesr and pharmaceutically-acceptable salts thereof.

Particular compounds of the invention are R-isomers of compounds of formula I in accord with formula VII,

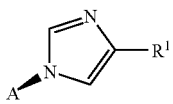

VII wherein A and $R^1$ are as defined for compounds of formula I.

Other particular compounds of the invention are those of formula VII wherein A is of formula II and $R^1$ is as defined for compounds of formula I.

Other particular compounds of the invention include those of formula I wherein E represents a single bond; or an enantiomer thereof, and pharmaceutically-acceptable salts thereof.

Particular compounds of the invention encompass those of formula I wherein $Ar^1$ is selected from phenyl or thiophenyl having optional substituents as defined herein and D is morpholino.

Other particular compounds of the invention encompass those of formula I wherein $Ar^1$ is selected from phenyl or thiophenyl and $Ar^2$ is selected from hydrogen, halogen, phenyl, furanyl or thiophenyl having optional substituents as defined herein.

Particular compounds of the invention are those described herein and pharmaceutically-acceptable salts thereof.

In a further aspect the invention relates to compounds according to formula I wherein one or more of the atoms is a radioisotope of the same element. In a particular form of this aspect of the invention the compound of formula I is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation-with tritium gas in the presence of a palladium catalyst, or (2) exchange of hydrogen for tritium performed in the presence of tritium gas and a suitable organometallic (e.g. palladium) catalyst.

Compounds of the invention labeled with tritium are useful for the discovery of novel medicinal compounds which bind to and modulate the activity, by agonist, partial agonist, or antagonism, of the α7 nicotinic acetylcholine receptor. Such tritium-labeled compounds may be used in assays that measure the displacement of a such compounds to assess the binding of ligand that bind to α7 nicotinic acetylcholine receptors.

In another aspect the invention relates to compounds according to formula I and their use in therapy and to compositions containing them.

In another aspect the invention encompasses the use of compounds according to formula I for the therapy of diseases mediated through the action of nicotinic acetylcholine receptors. A more particular aspect of the invention relates to the use of compounds of formula I for the therapy of diseases mediated through the action of α7 nicotinic acetylcholine receptors.

Another aspect of the invention encompasses a method of treatment or prophylaxis of diseases or conditions in which activation of the α7 nicotinic receptor is beneficial which method comprises administering a therapeutically-effective amount of a compound of the invention to a subject suffering from said disease or condition.

One embodiment of this aspect of the invention is a method of treatment or prophylaxis, wherein the disorder is anxiety, schizophrenia, mania or manic depression.

Another embodiment of this aspect of the invention is a method of treatment or prophylaxis of neurological disorders, psychotic disorders or intellectual impairment disorders, which comprises administering a therapeutically effective amount of a compound of the invention.

Another embodiment of this aspect of the invention is a method of treatment or prophylaxis, wherein the disorder is Alzheimer's disease, learning deficit, cognition deficit, attention deficit, memory loss, or Attention Deficit Hyperactivity Disorder.

Another embodiment of this aspect of the invention is a method of treatment or prophylaxis, wherein the disorder is Parkinson's disease, Huntington's disease, Tourette's syndrome, or neurodegenerative disorders in which there is loss of cholinergic synapses.

Another embodiment of this aspect of the invention is a method of treatment or prophylaxis of jetlag, nicotine addiction, craving, pain, and for ulcerative colitis, which comprises administering a therapeutically effective amount of a compound of the invention.

Yet another embodiment of this aspect of the invention is a method for inducing the cessation of smoking which comprises administering an effective amount of a compound of the invention.

Another embodiment of this aspect of the invention is a pharmaceutical composition comprising a compound of the invention and at least one pharmaceutically-acceptable excipient, diluent, lubricant or carrier.

A further aspect of the invention relates to a pharmaceutical composition useful for treating or preventing a condition or disorder mentioned herein arising from dysfunction of nicotinic acetylcholine receptor neurotransmission in a mammal, preferably a human, comprising an amount of a compound of formula I, an enantiomer thereof or a pharmaceutically-acceptable salt thereof, effective in treating or preventing such disorder or condition, and at least one pharmaceutically-acceptable excipient, diluent, lubricant or carrier.

Another embodiment of this aspect of the invention relates to use of a pharmaceutical composition of the invention for the treatment, amelioration or prophylaxis of human diseases or conditions in which activation of the α7 nicotinic receptor is beneficial.

Another embodiment of this aspect of the invention is the use of the pharmaceutical composition of the invention for the treatment or prophylaxis of neurological disorders, psychotic disorders or intellectual impairment disorders.

Another embodiment of this aspect of the invention is the use of the pharmaceutical composition of the invention for the treatment or prophylaxis of Alzheimer's disease, learning deficit, cognition deficit, attention deficit, memory loss, Attention Deficit Hyperactivity Disorder, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect of the invention is the use of a compound according to the invention, an enantiomer thereof or a pharmaceutically-acceptable salt thereof, in the manufacture of a medicament for the treatment or prophylaxis of the diseases or conditions mentioned herein.

Another embodiment of this aspect of the invention is the use of a compound of the invention in the manufacture of a medicament for the treatment or prophylaxis of human diseases or conditions in which activation of the α7 nicotinic receptor is beneficial.

Another embodiment of this aspect of the invention is the use of a compound of the invention in the manufacture of a medicament for the treatment or prophylaxis of neurological disorders, psychotic disorders or intellectual impairment disorders.

Another embodiment of this aspect of the invention is the use of a compound of the invention in the manufacture of a medicament for treatment or prophylaxis of Alzheimer's disease, learning deficit, cognition deficit, attention deficit, memory loss or Attention Deficit Hyperactivity Disorder.

Another embodiment of this aspect of the invention is the use of a compound of the invention in the manufacture of a medicament for treatment or prophylaxis of anxiety, schizophrenia, or mania or manic depression.

Another embodiment of this aspect of the invention is the use of a compound of the invention in the manufacture of a medicament for treatment or prophylaxis of Parkinson's disease, Huntington's disease, Tourette's syndrome, or neurodegenerative disorders in which there is loss of cholinergic synapses.

Another embodiment of this aspect of the invention is the use of a compound as described above in the manufacture of a medicament for the treatment or prophylaxis of jetlag, pain, or ulcerative colitis.

Another aspect of the invention relates to the use of a compound of the invention in the manufacture of a medicament for facilitating the cessation of smoking or the treatment of nicotine addiction or craving including that resulting from exposure to products containing nicotine.

For the uses, methods, medicaments and compositions mentioned herein the amount of compound used and the dosage administered will, of course, vary with the compound employed, the mode of administration and the treatment desired. However, in general, satisfactory results are obtained when the compounds of the invention are administered at a daily dosage of from about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carriers, lubricants and diluents.

The compounds of formula I, an enantiomer thereof, and pharmaceutically-acceptable salts thereof, may be used on their own or in the form of appropriate medicinal preparations for enternal or parenteral administration. According to a further aspect of the invention, there is provided a pharmaceutical composition including preferably less than 80% and more preferably less than 50% by weight of a compound of the invention in admixture with an inert pharmaceutically-acceptable diluent, lubricant or carrier. Examples of diluents, lubricants and carriers are:

for tablets and dragees: lactose, starch, talc, stearic acid;
for capsules: tartaric acid or lactose;
for injectable solutions: water, alcohols, glycerin, vegetable oils;
for suppositories: natural or hardened oils or waxes.

There is also provided a process for the preparation of such a pharmaceutical composition which process comprises mixing the ingredients.

Compounds according to the invention are agonists of nicotinic acetylcholine receptors. While not being limited by theory, it is believed that agonists of the α7 nicotinic acetylcholine receptor (nAChR) subtype are useful in the treatment or prophylaxis of neurological disorders, psychotic disorders and intellectual impairment disorders, and to have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of neurological disorders, psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain, chronic pain, and in the treatment or prophylaxis of Parkinson's disease, Huntington's disease, Tourette's syndrome, and neurodegenerative disorders in which there is loss of cholinergic synapses.

Compounds of the invention may further be useful for the treatment or prophylaxis of jetlag, for use in inducing the cessation of smoking, craving, and for the treatment or prophylaxis of nicotine addiction including that resulting from exposure to products containing nicotine.

It is also believed that compounds according to the invention are useful in the treatment and prophylaxis of ulcerative colitis.

The compounds of the invention have the advantage that they may be less toxic, be more efficacious, be longer acting, have a broader range of activity, be more potent, produce fewer side effects, are more easily absorbed or have other useful pharmacological properties when compared to known therapeutic moieties.

The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Methods of Preparation

Compounds of the invention may be prepared according to the synthetic schemes that follow, wherein A, D, E, $Ar^1$, and $Ar^2$ unless otherwise indicated, are as defined herein.

Method A-

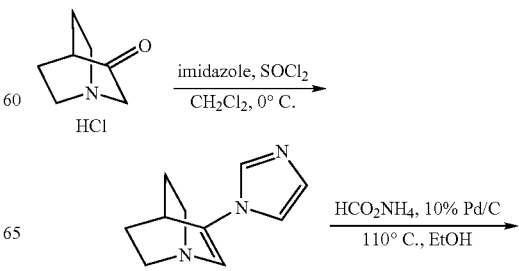

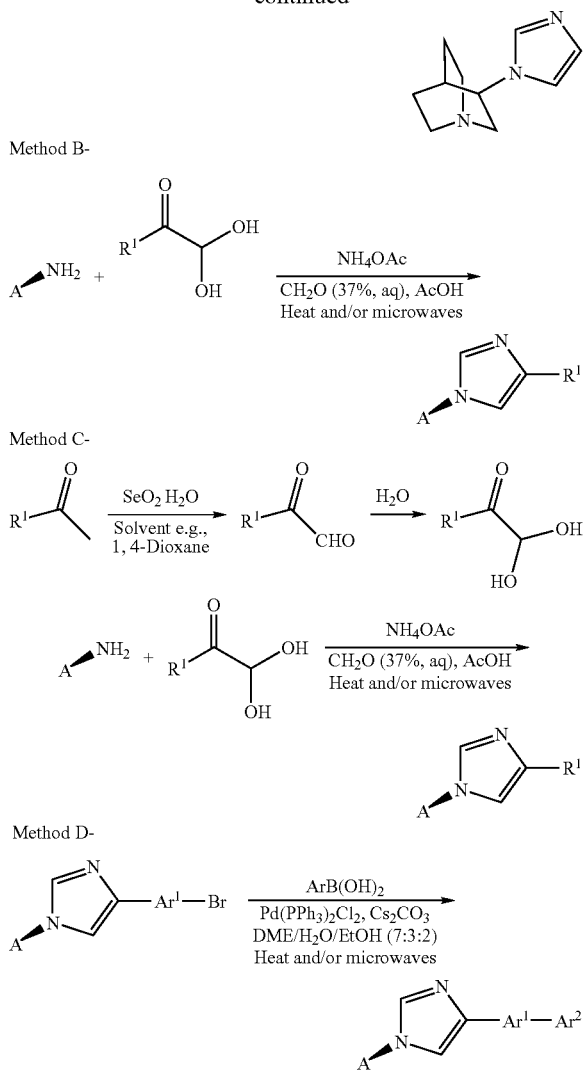

General Experimental Procedures and Definitions

Commercial reagents were used without further purification. Mass spectra were recorded using either a Hewlett Packard 5988A or a MicroMass Quattro-1 Mass Spectrometer and are reported as m/z for the parent molecular ion. Room temperature refers to 20-25° C.

$SiO_2$ chromatography was performed with an Isco CombiFlash Sq 16× instrument and pre-packaged disposable RediSep $SiO_2$ stationary phase columns (4, 12, 40, 120 gram sizes) with gradient elution at 5-125 mL/min of selected bi-solvent mixture, UV detection (190-760 nm range) or timed collection, 0.1 mm flow cell path length.

Microwave heating was achieved with a Personal Chemistry Smith Synthesizer or a Personal Chemistry Emrys Optimizer (monomodal, 2.45 GHz, 300 W max).

Supercritical Fluid Chromatography (SFC) was performed as a means of purification for selected compounds and intermediates.

Reverse Phase High Pressure Liquid Chromatography (RP-HPLC) was employed as a method of purification for selected compounds.

LC/MS HPLC method was generally performed with a Agilent Zorbax 5 μSB-C8 column 2.1 mm×5 cm. Solvents: A=$H_2O$ with 0.05% TFA, B=10% $H_2O$, 90% Acetonitrile, 0.05% TFA. Gradient: (10-90% B over 3 min., 90% B hold through 4 min., −10% B at 5 min. and hold at 10% B until 6 min).

Unless otherwise indicated, halo includes chloro, bromo, fluoro and iodo and halogen refers to fluorine, chlorine, bromine, or iodine; $C_{1-6}$alkyl includes methyl, ethyl and linear, cyclic or branched propyl, butyl, pentyl or hexyl; $C_{2-6}$alkenyl includes ethenyl, 1-propenyl, 2-propenyl or 3-propenyl and linear, branched or cyclic butenyl, pentenyl or hexenyl; $C_{2-6}$alkynyl includes ethynyl or propynyl; the $C_{1-4}$alkyl groups referred to herein, e.g., methyl, ethyl, n-propyl, n-butyl, i-propyl, i-butyl, t-butyl, s-butyl, whether alone or part of another group, may be straight-chained or branched, and the $C_{3-4}$alkyl groups may also be cyclic, e.g., cyclopropyl, cyclobutyl. Alkyl groups referred to herein may optionally have one, two or three halogen atoms substituted thereon.

Pharmaceutically-acceptable derivatives include solvates and salts. For example, the compounds of formula I can form acid addition salts with acids, such as the conventional pharmaceutically-acceptable acids, for example, maleic, hydrochloric, hydrobromic, phosphoric, acetic, fumaric, salicylic, citric, lactic, mandelic, tartaric and methanesulfonic acids.

Pharmacology

The pharmacological activity of the compounds of the invention may be measured in the tests set out below:

Test A—Assay for Affinity at $\alpha_7$ nAChR Subtype

125I-α-Bungarotoxin (BTX) binding to rat hippocampal membranes. Rat hippocampi are homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate is centrifuged for 5 minutes at 1000 g, the supernatant is saved and the pellet re-extracted. The pooled supernatants are centrifuged for 20 minutes at 12,000 g, washed, and re-suspended in HB. Membranes (30-80 μg) are incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pre-treating the filters for 3 hours with 1% (BSA/0.01% PEI (polyethyleneimine) in water is critical for low filter blanks (0.07% of total counts per minute). Non-specific binding is described by 100 μM (−)-nicotine, and specific binding is typically 75%.

Test B—Assay for Affinity to the $\alpha_4$ nAChR Subtype

[$^3$H]-(−)-nicotine binding. Using a procedure modified from Martino-Barrows and Kellar (Mol Pharm (1987) 31:169-174), rat brain (cortex and hippocampus) is homogenised as in the [$^{125}$I]α-BTX binding assay, centrifuged for 20 minutes at 12,000×g, washed twice, and then re-suspended in HB containing 100 μM diisopropyl fluorophosphate. After 20 minutes at 4° C., membranes (approximately 0.5 mg) are incubated with 3 nM [$^3$H]-(−)-nicotine, test drug, 1 μM atropine, and either 2 mM $CaCl_2$ or 0.5 mM EGTA for 1 hour at 4° C., and then filtered over Whatman glass fibre filters (thickness C) (pre-treated for 1 hour with 0.5% PEI) using a Brandel cell harvester. Non-specific binding is described by 100 μM carbachol, and specific binding is typically 84%.

Binding Data Analysis for Tests A and B $IC_{50}$ values and pseudo Hill coefficients ($n_H$) are calculated using the non-linear curve fitting program ALLFIT (DeLean A, Munson P J and Rodbard D (1977) Am. J. Physiol., 235:E97-E102). Saturation curves are fitted to a one site model, using the non-linear regression program ENZFITTER (Leatherbarrow, R. J. (1987)), yielding $K_D$ values of 1.67 and 1.70 nM for the [$^{125}$I]-α-BTX and [$^{3}$H]-(−)-nicotine ligands respectively. $K_i$ values are estimated using the general Cheng-Prusoff equation:

$$K_i = [IC_{50}]/((2+([ligand]/K_D])^n)^{1/n}-1)$$

where a value of n=1 is used whenever $n_H$<1.5 and a value of n=2 is used when $n_H$≧1.5. Samples are assayed in triplicate and are typically ±5%. $K_i$ values are determined using 6 or more drug concentrations.

Compounds of the invention generally have binding affinities ($K_i$) of less than 10 μM in either Test A and or Test B.

EXAMPLES

The following examples are non-limiting and embody particular aspects of the invention.

Example 1

3-Imidazol-1-yl-1-azabicyclo[2.2.2]octane

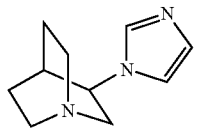

a) 3-Imidazol-1-yl-1-azabicyclo[2.2.2]oct-2-ene

To a solution of imidazole (6.53 g, 96 mmol) in anhydrous CH$_2$Cl$_2$ (50 mL) at 0° C. under a nitrogen atmosphere was added thionyl chloride (2.1 mL, 28.8 mmol) dropwise, resulting in a fine white precipitate. After 15 minutes the mixture was added to 3-quinuclidone hydrochloride salt (2.59 g, 16 mmol) in anhydrous CH$_2$Cl$_2$ (50 mL) under an inert atmosphere at 0° C. The mixture was allowed to warm to ambient temperature, stirred for 2 days, then neutralized with saturated NaHCO$_3$ (aq), adjusted to pH~12 by the addition of 10% NaOH (aq) and extracted into CH$_2$Cl$_2$ (3×100 mL). The combined organic extracts were dried over Na$_2$SO$_4$, filtered and concentrated in vacuo. The residue was subjected to flash chromatography (SiO2—40 grams; gradient elution: 1-10% 3N NH$_3$/MeOH—CH$_2$Cl$_2$ at 50 mL/min over 40 min) to afford the title compound (1a) as an orange-yellow tacky solid (640 mg, 23%). Mass spectrum (ES+): M+1: 176 (100%); $^1$H NMR (300 MHz, CDCl$_3$) δ 1.72 (m, 2H), 1.79 (m, 2H), 2.69 (m, 2H), 3.02 (m, 2H), 3.26 (m, 1H), 6.53 (d, J=2 Hz, 1H), 7.11 (s, 1H), 7.15 (s, 1H), 7.71 (s, 1H).

b) 3-Imidazol-1-yl-1-azabicyclo[2.2.2]octane

To a mixture of 3-imidazol-1-yl-1-azabicyclo[2.2.2]oct-2-ene (1a) (356 mg, 2.03 mmol) and ammonium formate (2.6 g, 40.6 mmol) in absolute EtOH (6 mL) was added 10% Pd/C (178 mg, 50% w/w). The sealed reaction vessel was heated to 110° C. for 13 hrs before cooling to ambient temperature. The mixture was filtered through diatomaceous earth (0.75" by 2" diameter), washed liberally with EtOH and concentrated to a white-yellow tacky residue which was subsequently purified by flash chromatography (SiO$_2$—40 grams; gradient elution: 5-30% 3N NH$_3$/MeOH—EtOAc at 60 mL/min over 25 min) to yield the title compound (188 mg, 52%). Mass spectrum (ES+): M+1: 178 (100%); $^1$H NMR (300 MHz, CDCl$_3$) δ 1.50 (m, 1H), 1.64 (m, 1H), 1.77 (m, 2H), 2.09 (app q, J=3 Hz, 1H), 2.81-3.05 (m, 4H), 3.15 (dd, J=14.5, 4.4 Hz, 1H), 3.47 (ddd, J=14.5, 9.7, 1.8 Hz, 1H), 4.26 (m, 1H), 7.05 (s, 1H), 7.08 (s, 1H), 7.62 (s, 1H).

Example 2

(R)-3-(4-phenyl-imidazol-1-yl)-1-azabicyclo[2.2.2]octane

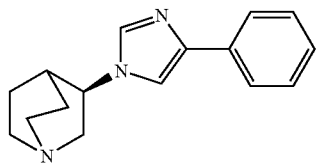

A cone shaped thick-walled glass vial was charged with a stir bar, (R)-(+)-3-aminoquinuclidine dihydrochloride (97 mg, 0.48 mmol), ammonium acetate (75 mg, 0.97 mmol), phenylglyoxal monohydrate (73 mg, 0.48 mmol), formaldehyde (37%, aqueous—35 μL, 0.48 mmol) and glacial AcOH (1 mL). The vials were sealed and subjected to microwave radiation for 10 minutes at 120° C. The resultant mixture was dilute with EtOAc (1×20 mL) and basified to pH~13 with 10% NaOH (aq), extracted with EtOAc (3×20 mL), dried over Na$_2$SO$_4$ (s), filtered, and concentrated by rotary evaporation to an orange solid. The material was subjected to flash chromatography (SiO$_2$—12 grams; gradient elution: 1-8% 3 N NH$_3$/MeOH—CH$_2$Cl$_2$ at 20 mL/min over 30 min) to provide a 5:1 regio-isomeric mixture as determined by $^1$H NMR signal integration of the 5- and 4-phenyl-imidazol-1-yl compounds as orange-yellow crystals (50 mg, 41%). The mixture was subsequently purified by SFC: Berger Cyano column (6 μm particle size, 21 mm ID×150 cm), 15-30% MeOH/CO$_2$ at 50 mL/min, to give (R)-3-(4-phenyl-imidazol-1-yl)-1-azabicyclo[2.2.2]octane (Example 3) as a white tacky gum (6 mg, 5%). Mass spectrum (ES+): M+1: 254 (100%); $^1$H NMR (300 MHz, CDCl$_3$) δ 1.53 (m, 1H), 1.68-2.01 (m, 3H), 2.15 (app q, J=3.1 Hz, 1H), 2.74 (m, 1H), 2.82-3.0 (m, 3H), 3.19(dd, J=14.5, 5.2 Hz, 1H), 3.50 (ddd, J=14.5, 7.7, 2.2 Hz, 1H), 4.26 (m, 1H), 7.24 (m, 1H), 7.31 (d, J=1.3 Hz, 1H), 7.37 (m, 2H), 7.64 (d, J=1.3 Hz, 1H), 7.77 (d, J=7 Hz, 2H).

Example 3

(R)-3-[4-(4-morpholin-4-yl-phenyl)-imidazol-1-yl]-1-azabicyclo[2.2.2]octane

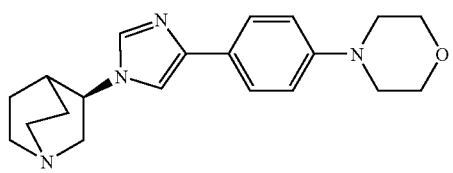

The compound of Example 3 was prepared by a process analogous to that of Example 2 utilizing 4-morpholinophenylgiyoxal hydrate in place of phenylglyoxal monohydrate, employing SFC chromatography with 20% MeOH/CO₂ with 0.5% DMEA at 50 mL/min, monitoring at 280 nm, to separate the regioisomeric mixture.

(R)-3-[4-(4-Morpholin-4-yl-phenyl)-imidazol-1-yl]-1-azabicyclo[2.2.2]octane (Example 5) was obtained as a pale yellow film (1.1 mg, 0.4%). Mass spectrum (ES+): M+1: 339 (100%); ¹H NMR (300 MHz, CDCl₃) δ 1.53 (m, 2H), 1.68-1.84 (m, 3H), 2.14 (app q, J=2.9 Hz, 1H), 2.84-3.05 (m, 4H), 3.18 (app t, J=4.9 Hz, 4H), 3.49 (ddd, J=14.3, 9.9, 2.0 Hz, 1H), 3.88 (app t, J=4.9 Hz, 4H), 4.24 (m, 1H), 6.93 (d, J=8.8 Hz, 2H), 7.21 (d, J=1.1 Hz, 1H), 7.61 (d, J=1.1 Hz, 1H), 7.68 (d, J=8.8 Hz, 2H).

Example 4

(R)-3-[4-(5-bromo-thiophen-2-yl)-imidazol-1-yl]-1-azabicyclo[2.2.2]octane

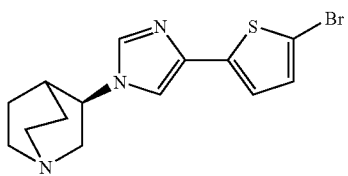

a) 1-(5-Bromo-thiophen-2-yl)-2,2-dihydroxyethanone

A mixture of selenium dioxide (8.66 g, 78 mmol), water (2.8 mL) and 1,4-dioxane (75 mL) was heated to reflux to dissolve all particulates (~15 min) before the addition of 2-acetyl-5-bromothiophene (8 g, 39 mmol) in one portion. After refluxing for 15 hrs, the mixture was cooled to ambient temperature, filtered through diatomaceous earth (1.5" by 3" diameter), washed liberally with Et₂O, and concentrated in vacuo to a yellow residue. The residue was subjected to Kugelrohr distillation (150° C./1 Torr) to yield a glyoxal as a yellow oil, which was immediately added to boiling water. Recrystallization from water, filtration, and drying (37° C. and 5 Torr) yielded the glyoxal hydrate, 1-(5-bromo-thiophen-2-yl)-2,2-dihydroxyethanone, as white-pink needles (6.723 g, 73%). ¹H NMR (300 MHz, DMSO-d₆) δ 5.43 (t, J=6.1 Hz, 1H), 6.93 (d, J=6.1 Hz, 2H), 7.37 (d, J=4.1 Hz, 1H), 7.81 (d, J=4.1 Hz, 1H); ¹³C NMR (300 MHz, DMSO-d₆) δ 90.28, 122.32, 132.23, 135.73, 141.15, 189.6.

b) (R)-3-[4-(5-Bromo-thiophen-2-yl)-imidazol-1-yl]-1-azabicyclo[2.2.2]octane

Five individual round-bottomed thick-walled glass vials were charged with stir bars, (R)-(+)-3-aminoquinuclidine dihydrochloride (440 mg, 2.21 mmol), ammonium acetate (195 mg, 2.53 mmol), 1-(5-bromo-thiophen-2-yl)-2,2-dihydroxyethanone (500 mg, 2.21 mmol), formaldehyde (37%, aqueous—210 μL, 2.53 mmol) and glacial AcOH/water (1:1, 3.5 mL). All vials were crimp sealed and subjected to microwave radiation for 20 minutes at 120° C. The resultant mixtures were combined, diluted with water, basified to pH~13 with 20% NaOH (aq), and extracted with CHCl₃ (5×60 mL) and EtOAc (2×40 mL). The combined organic extracts were dried over MgSO₄, filtered, and concentrated by rotary evaporation to a brown gummy residue. The material was subjected to flash chromatography (SiO₂—120 grams; gradient elution: 5-10% 4N NH₃/MeOH—EtOAc at 90 mL/min over 48 min) to provide a ~2:1 regio-isomeric mixture of 5- and 4-bromothienyl-imidazolyl compounds as an orange-tan gum (1.186 g, 33%) as determined by ¹H NMR signal integration. The mixture was subsequently purified by SFC with 25% MeOH/CO₂ with 0.5% DMEA at 50 mL/min, monitoring at 280 nm, to give (R)-3-[4-(5-bromo-thiophen-2-yl)-imidazol-1-yl]-1-azabicyclo[2.2.2]octane (Example 6) was obtained as a pale orange solid (283 mg, 8%). Mass spectrum (API+) M+1: 338 (100%); ¹H NMR (300 MHz, CDCl₃) δ 1.53 (m, 1H), 1.63-1.87 (m, 3H), 2.13 (app q, J=3.1 Hz, 1H), 2.81-3.04 (m, 4H), 3.14 (dd, J=14.5, 5.3 Hz, 1H), 3.48 (ddd, J=14.5, 9.7, 1.8 Hz, 1H), 4.22 (m, 1H), 6.97 (app q, J=4 Hz, 2H), 7.15 (d, J=1.3 Hz, 1H), 7.57 (d, J=1.3 Hz, 1H).

Example 5

(R)-3-[4-(5-Phenyl-thiophen-2-yl)-imidazol-1-yl]-1-azabicyclo[2.2.2]octane

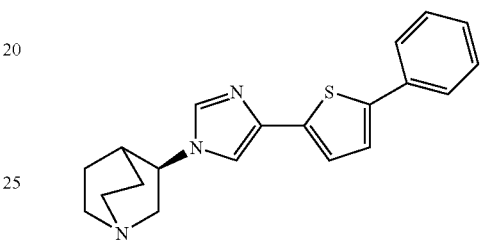

A conical thick-walled glass vial was charged with a stir bar, (R)-3-[4-(5-bromo-thiophen-2-yl)-imidazol-1-yl]-1-azabicyclo[2.2.2]octane (40 mg, 0.12 mmol), phenylboronic acid (17 mg, 0.14 mmol), dichlorobis(triphenylphosphine)-palladium (II) (4.2 mg, 0.006 mmol), Cs₂CO₃ (78 mg, 0.24 mmol) and DME/H₂O/EtOH (7:3:2—1 mL). The vial was crimp sealed and subjected to microwave radiation for 18 minutes at 150° C. The resultant black slurry was filtered through a 0.7 μm GMF filter, washing with MeOH (2×1 mL) and subjected to RP-HPLC purification (gradient elution: 5-25% acetonitrile over 30 minutes at 24 mL/min—desired compound elutes at 26 minutes). The appropriate fractions were concentrated via centrifugal evaporation to form the bis-trifluoroacetic acid salt and subsequently dissolved in MeOH, neutralized with saturated K₂CO₃ (aq) and extracted with EtOAc (5×8 mL). The combined organic extracts were dried over MgSO₄, concentrated via rotary evaporation and excess 1 N HCl in Et₂O added. The resultant salt was triturated with Et₂O, collected by filtration and dried to afford the title compound, as the blue-green dihydrochloride salt (40 mg, 81%). Mass spectrum (API+) M+1: 336 (100%); ¹H NMR (300 MHz, MeOH-d₄) δ 2.05 (m, 2H), 2.24 (m, 2H), 2.71 (m, 1H), 3.39-3.56 (m, 3H), 3.61 (m, 1H), 3.90 (ddd, J=14.0, 7.9, 1.7 Hz, 1H), 4.11 (ddd, J=14.0, 10.5, 2.6 Hz, 1H), 5.14 (m, 1H), 7.32-7.47 (m, 4H), 7.52 (d, J=4 Hz, 1H), 7.69 (d, J=7 Hz, 2H), 8.15 (d, J=1.3 Hz, 1H), 9.24 (d, J=1.3 Hz, 1H).

Example 6

3-((R)-4-Thiophen-2-yl-imidazol-1-yl)-1-azabicyclo[2.2.2]octane

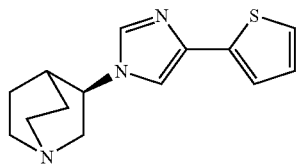

In the procedure described in Example 5 (R)-3-(4-thiophen-2-yl-imidazol-1-yl)-1-azabicyclo[2.2.2]octane was obtained as a by-product (Example 6) under the reaction conditions employed. The compound was purified by RP-HPLC (eluted at 10 minutes) to afford the bis-trifluoroacteic acid salt of title compound as a clear, yellow gum. Mass spectrum (API+) M+1: 260 (100%); $^1$H NMR (300 MHz, MeOH-d$_4$) δ 2.03 (m, 2H), 2.21 (m, 2H), 2.65 (m, 1H), 3.40-3.51 (m, 3H), 3.59 (m, 1H), 3.87 (ddd, J=13.8, 6.0, 1.9 Hz, 1H), 4.05 (ddd, J=13.8, 9.9, 2.4 Hz, 1H), 5.04 (m, 1H), 7.14 (dd, J=5.1, 3.7 Hz, 1H) 7.45 (dd, J=3.7, 1 Hz, 1H), 7.51 (dd, J=5.1, 1 Hz, 1H), 7.94 (d, J=1.3 Hz, 1H), 8.75 (d, J=1.3 Hz, 1H).

4-Substituted compounds of the following structure prepared by methods analogous to those used in Example 7 are illustrated in Table 1:

TABLE 1

| Example # | "R$^1$" Group | LC/MS retention time (min) | MS (M + 1) ion |
|---|---|---|---|
| 7 | | 1.51 | 342 |
| 8 | | 1.40 | 342 |
| 9 | | 1.27 | 326 |
| 10 | | 0.67 | 337 |
| 11 | | 0.76 | 337 |

The invention claimed is:

1. A compound according to formula I:

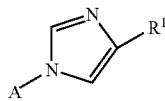

I wherein:

A represents:

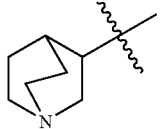

II

-continued

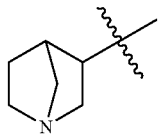

III

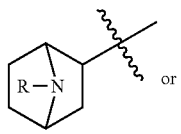

IV or

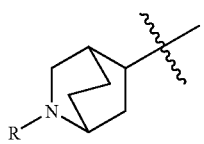

V where R represents hydrogen or methyl, and

R$^1$ represents hydrogen or a moiety of Formula VI

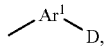

VI wherein:

Ar$^1$ is selected from a 5- or 6-membered aromatic or heteroaromatic ring having 0, 1 or 2 nitrogen atoms, 0 or 1 oxygen atoms, and 0 or 1 sulfur atoms, or selected from an 8-, 9- or 10-membered fused aromatic or heteroaromatic ring system having 0, 1, 2 or 3 nitrogen atoms, 0 or 1 oxygen atoms, and 0 or 1 sulfur atoms;

D is selected from hydrogen, NR$^2$R$^3$, or E-Ar$^2$;

wherein

E is a single bond, —O—, —S—, or —NR$^3$—;

Ar$^2$ is selected from a 5- or 6-membered aromatic or heteroaromatic ring having 0, 1 or 2 nitrogen atoms, 0 or 1 oxygen atoms, and 0 or 1 sulfur atoms;

where each Ar$^1$ or Ar$^2$ moiety may be unsubstituted or bear 1, 2 or 3 substituents selected from —R$^3$, —C$_1$-C$_6$alkyl, —C$_2$-C$_6$alkenyl, —C$_2$-C$_6$alkynyl, halogen, —CN, —NO$_2$, —CF$_3$, —S(O)$_n$R$^3$, —NR$^2$R$^3$, —CH$_2$NR$^2$R$^3$, —OR$^3$, —CH$_2$OR$^3$ or —CO$_2$R$^4$;

R$^2$ and R$^3$ are independently selected at each occurrence from hydrogen, —C$_1$-C$_4$alkyl, aryl, heteroaryl, —C(O)R$^4$, —C(O)NHR$^4$, —CO$_2$R$^4$ or —SO$_2$R$^4$, or R$^2$ and R$^3$ in combination is —(CH$_2$)$_j$G(CH$_2$)$_k$— wherein G is oxygen, sulfur, NR$^4$, or a bond;

j is 2, 3 or 4;

k is 0, 1 or 2;

n is 0, 1 or 2, and

R$^4$ is independently selected at each occurrence from hydrogen, —C$_{1-4}$alkyl, aryl, or heteroaryl;

and stereoisomers, enantiomers, in vivo-hydrolysable precursors and pharmaceutically-acceptable salts thereof.

2. A compound according to claim 1 wherein:
A represents:

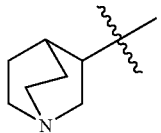
II

R¹ represents hydrogen or a moiety of Formula VI

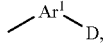
VI wherein:
Ar¹ is selected from a 5- or 6-membered aromatic or heteroaromatic ring having 0 or 1 nitrogen atoms, 0 or 1 oxygen atoms, and 0 or 1 sulfur atoms;
D is selected from hydrogen, NR²R³, or E-Ar²;
wherein:
E is a single bond, —O—, —S—, or —NR³—;
Ar² is selected from a 5- or 6-membered aromatic or heteroaromatic ring having 0 or 1 nitrogen atoms, 0 or 1 oxygen atoms, and 0 or 1 sulfur atoms;
where each Ar¹ or Ar² moiety may be unsubstituted or bear 1, 2 or 3 substituents selected from halogen, —CN, —NO₂, —CF₃, —CH₃ or —C₂H₅;
R² and R³ are independently selected at each occurrence from hydrogen, —C₁-C₄alkyl, aryl, heteroaryl, or R² and R³ in combination is —(CH₂)ⱼG(CH₂)ₖ— wherein G is oxygen;
j is 2, 3 or 4;
k is 0, 1 or 2;
and stereoisomers, enantiomers, in vivo-hydrolysable precursors and pharmaceutically-acceptable salts thereof.

3. A compound according to claim 1, wherein A represents:

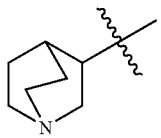
II or an enantiomer thereof, and pharmaceutically-acceptable salts thereof.

4. A compound according to claim 1, wherein said compound is an R-isomer in accord with formula VII,

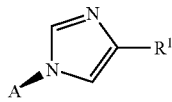
VII wherein A and R¹ are as defined for compounds of formula I.

5. A compound according to claim 4, wherein A is of formula II

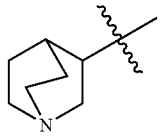
II and R¹ is as defined for compounds of formula I.

6. A compound according to claim 1, wherein E represents a single bond; or an enantiomer thereof, and pharmaceutically-acceptable salts thereof.

7. A compound according to claim 1, wherein Ar¹ is selected from phenyl or thiophenyl and D is morpholino.

8. A compound according to claim 1, wherein Ar¹ is selected from phenyl or thiophenyl and Ar² is selected from hydrogen, halogen, phenyl, furanyl or thiophenyl having optional substituents.

9. A compound according to claim 1, wherein one or more of the atoms is a radioisotope of the same element.

10. A pharmaceutical composition comprising a compound according to claim 1 and a pharmaceutically-acceptable diluent, lubricant or carrier.

* * * * *